(12) United States Patent
Boyd et al.

(10) Patent No.: US 8,287,843 B2
(45) Date of Patent: Oct. 16, 2012

(54) ANTIPLAQUE ORAL CARE COMPOSITIONS

(75) Inventors: Thomas J. Boyd, Metuchen, NJ (US);
Guofeng Xu, Princeton, NJ (US); Abdul Gaffar, Princeton, NJ (US); David B. Viscio, Monmouth Junction, NJ (US)

(73) Assignee: Colgate-Palmolive Company, New York, NY (US)

( * ) Notice: Subject to any disclaimer, the term of this patent is extended or adjusted under 35 U.S.C. 154(b) by 407 days.

(21) Appl. No.: 11/375,346

(22) Filed: Mar. 14, 2006

(65) Prior Publication Data

US 2006/0193791 A1  Aug. 31, 2006

Related U.S. Application Data

(63) Continuation-in-part of application No. 10/601,473, filed on Jun. 23, 2003, now abandoned, and a continuation-in-part of application No. 10/601,474, filed on Jun. 23, 2003, now abandoned, and a continuation-in-part of application No. 10/601,478, filed on Jun. 23, 2003, now abandoned, and a continuation-in-part of application No. 10/601,477, filed on Jun. 23, 2003, now abandoned, and a continuation-in-part of application No. 10/875,059, filed on Jun. 23, 2004, now abandoned.

(51) Int. Cl.
 *A61K 8/00* (2006.01)
(52) U.S. Cl. .......................................... 424/49; 424/54
(58) Field of Classification Search .................. 424/49, 424/54
See application file for complete search history.

(56) References Cited

U.S. PATENT DOCUMENTS

| | | | |
|---|---|---|---|
| 3,151,027 A | 9/1964 | Broge et al. | |
| 3,825,560 A | 7/1974 | Saito et al. | |
| 4,022,881 A * | 5/1977 | Hawking | 424/52 |
| 4,097,604 A * | 6/1978 | Thiele | 514/560 |
| 4,098,878 A * | 7/1978 | Baines et al. | 424/52 |
| 4,110,083 A | 8/1978 | Benedict | |
| 4,118,472 A | 10/1978 | Gaffar et al. | |
| 4,157,387 A | 6/1979 | Benedict | |
| 4,198,392 A | 4/1980 | Juneja | |
| 4,225,579 A | 9/1980 | Kleinberg | |
| 4,255,579 A | 3/1981 | Michne | |
| 4,469,674 A * | 9/1984 | Shah et al. | 424/52 |
| 4,477,428 A | 10/1984 | Silbering et al. | |
| 4,499,067 A | 2/1985 | Silbering et al. | |
| 4,499,068 A | 2/1985 | Silbering et al. | |
| 4,567,174 A | 1/1986 | Edwards et al. | |
| 4,670,592 A | 6/1987 | Eakin et al. | |
| 4,695,463 A | 9/1987 | Yang et al. | |
| 4,837,008 A | 6/1989 | Rudy et al. | |
| 5,180,577 A | 1/1993 | Polefka et al. | |
| 5,185,155 A | 2/1993 | Behan et al. | |
| 5,266,306 A | 11/1993 | Ohtsuki et al. | |
| 5,472,493 A | 12/1995 | Regan | |
| 5,597,553 A * | 1/1997 | Baffelli et al. | 424/49 |
| 5,695,745 A | 12/1997 | Barton et al. | |
| 5,780,015 A | 7/1998 | Fisher et al. | |
| 5,874,068 A | 2/1999 | Engelman et al. | |
| 5,989,524 A | 11/1999 | Dromard et al. | |
| 6,086,648 A * | 7/2000 | Rossetti et al. | 51/304 |
| 6,149,903 A | 11/2000 | Holt et al. | |
| 6,177,096 B1 | 1/2001 | Zerbe et al. | |
| 6,228,347 B1 | 5/2001 | Hersh | |
| 6,290,933 B1 | 9/2001 | Durga et al. | |
| 6,419,903 B1 | 7/2002 | Xu et al. | |
| 6,447,758 B1 | 9/2002 | Carale et al. | |
| 6,479,036 B1 | 11/2002 | Stanier et al. | |
| 6,685,921 B2 | 2/2004 | Lawlor | |
| 2002/0068039 A1 | 6/2002 | Pan et al. | |
| 2003/0133883 A1 | 7/2003 | Finnegan et al. | |
| 2003/0206874 A1 | 11/2003 | Doyle et al. | |
| 2004/0258629 A1 | 12/2004 | Boyd et al. | |
| 2004/0258630 A1 | 12/2004 | Boyd et al. | |
| 2004/0258631 A1 | 12/2004 | Boyd et al. | |
| 2004/0258632 A1 | 12/2004 | Boyd et al. | |
| 2005/0027001 A1 | 2/2005 | Boyd et al. | |

FOREIGN PATENT DOCUMENTS

| | | |
|---|---|---|
| EP | 0125827 | 11/1984 |
| EP | 0126558 | 11/1984 |
| EP | 0422803 | 4/1991 |
| EP | 0485616 | 5/1992 |
| FR | 2143557 | 2/1973 |
| GB | 1352420 | 5/1974 |
| GB | 1549074 | 7/1979 |
| GB | 2210264 | 6/1989 |
| HU | 176671 | 4/1981 |
| JP | 51023571 | 7/1976 |

(Continued)

OTHER PUBLICATIONS

G. R. O'Shea Company (Vertellus™; Castor Oil and its Chemistry).*
Tsumura, Yukako et al., "Antiplaque anticaries dentifrice compositions containing cationic microbicides" XP002309055, Nov. 4, 1997.
Lin, Chinling et al., "Dentrifrices containing cationic microbicides and nonionic surfactants dentifrices containing cationic microbicides and nonionic surfactants" XP 002309056, Sep. 21, 1999.
Tetronic 901 Block Copolymer—Technical Bulletin, 2004, BASF, cited in European Patent Appln. No. 04755903.4 in Notice of Opposition dated May 8, 2008.

(Continued)

Primary Examiner — Frederick Krass
Assistant Examiner — Chris Simmons
(74) Attorney, Agent, or Firm — Howard C. Lee

(57) ABSTRACT

The invention provides oral compositions including a safe and effective amount of a compound represented by the formula (I):

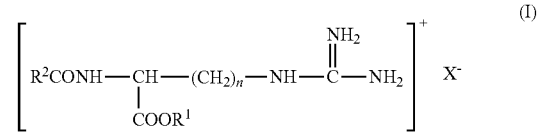

wherein $R^1$ and $R^2$ are independently selected from a hydrogen atom and an alkyl group and $X^-$ is an anion, and n is an integer of 1 to 25; and (b) a surfactant.

23 Claims, No Drawings

FOREIGN PATENT DOCUMENTS

| | | |
|---|---|---|
| JP | 56009211 | 1/1981 |
| JP | 60092208 | 5/1985 |
| JP | 61056214 | 12/1986 |
| JP | H3-291211 | 12/1991 |
| JP | 04005221 | 1/1992 |
| JP | 04036230 | 2/1992 |
| JP | 06084293 | 10/1994 |
| JP | 09286712 | 11/1997 |
| JP | 11255629 | 9/1999 |
| JP | 2000256155 | 9/2000 |
| WO | WO 91/18585 | 12/1991 |
| WO | WO 97/32565 | 9/1997 |
| WO | WO 98/50005 | 11/1998 |
| WO | WO 99/13734 | 3/1999 |
| WO | WO 99/29289 | 6/1999 |
| WO | WO 99/63958 | 12/1999 |
| WO | WO 03/013453 | 2/2003 |
| WO | WO 03/013454 | 2/2003 |
| WO | 03037285 A1 | 5/2003 |
| WO | WO 03/034842 | 5/2003 |
| WO | WO 03/043593 | 5/2003 |
| WO | WO 03/072039 | 9/2003 |

OTHER PUBLICATIONS

Kirk-Othmer, "Encyclopedia of Chemical Technology, vol. 22, Surfactants and Detersive Systems" Wiley-Interscience, 1983, Ed. 3rd.

* cited by examiner

ANTIPLAQUE ORAL CARE COMPOSITIONS

CROSS REFERENCE TO RELATED APPLICATIONS

This application is a continuation-in-part of each of the following: U.S. patent application Ser. No. 10/601,473 now abandoned, U.S. patent application Ser. No. 10/601,474 now abandoned, U.S. patent application Ser. No. 10/601,477 now abandoned, U.S. patent application Ser. No. 10/601,478 now abandoned, each filed Jun. 23, 2003; and U.S. patent application Ser. No. 10/875,059 now abandoned, filed Jun. 23, 2004; the contents of each of which are incorporated herein by reference.

BACKGROUND OF THE INVENTION

Dental plaque is present to some degree in the form of a film on virtually all dental surfaces. It is a byproduct of microbial growth, and comprises a dense microbial layer consisting of a mass of microorganisms embedded in a polysaccharide matrix. It is reported that plaque adheres firmly to dental surfaces and is removed only with difficulty even through a rigorous brushing regimen. Moreover, plaque rapidly re-forms on the tooth surface after it is removed. Plaque may form on any part of the tooth surface, and is found particularly at the gingival margin, in cracks in the enamel, and on the surface of dental calculus. The problem associated with the formation of plaque on the teeth lies in the tendency of plaque to build up and eventually produce gingivitis, periodontitis and other types of periodontal disease, as well as dental caries, bad breath (halitosis) and dental calculus.

As plaque is formed by oral bacteria, a wide variety of antibacterial agents have been proposed to retard plaque formation and the oral infections associated with plaque formation. For example, halogenated hydroxydiprrehyl ether compounds such as triclosan are well known to the art for their antibacterial activity and have been used in oral compositions to counter plaque formation by bacterial accumulation in the oral cavity. However, these antibacterial agents which work to reduce plaque formation by temporary reduction in the population of oral bacteria have numerous disadvantages when incorporated into commercial products, including disadvantages stemming from production costs and logistics, regulatory frameworks of various jurisdictions, stability of commercially acceptable formulations, etc.

Thus, there remains a need in the art for oral compositions that reduce or prevent plaque formation.

BRIEF SUMMARY OF THE INVENTION

The invention provides oral compositions including a safe and effective amount of a compound represented by the formula (I):

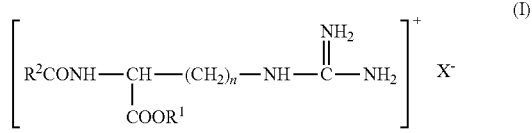

wherein $R^1$ and $R^2$ are independently selected from a hydrogen atom and an alkyl group and $X^-$ is an anion, and n is an integer of 1 to 25; and (b) a surfactant.

DETAILED DESCRIPTION OF THE INVENTION

The invention provides an oral care composition that contains the compound represented by formula (I):

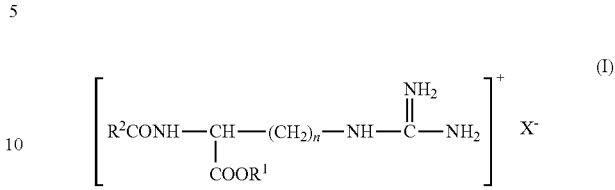

wherein $R^1$ and $R^2$ are independently selected from a hydrogen atom and an alkyl group.

In various embodiments, $R^1$ is independently selected from an alkyl group 1 to 25 carbon atoms, preferably 1 to 8 carbon atoms, most preferably 2, 3, 4, 5, 6, or 7 carbon atoms. In various embodiments, $R^2$ is may be an alkyl group having 1 to 50 carbon atoms, preferably 1 to 30 carbon atoms. The symbol "n" may be an integer of 1 to 10, preferably n is 3.

The group $X^-$ may be an anion such that resultant ester salts is, for example, a an inorganic acid salt such as a hydrochloride, or a sulfate or an organic salt such as acetate, tartarate or citrate.

In various embodiments, $R^2CO$ may be derived from a natural system mixed fatty acid residue such as coconut oil fatty acids, tallow fatty acids, or a mono-fatty acid residue such a lauroyl, myristyl, stearoyl and the like, the lauroyl group being preferred.

Examples of antibacterial ester compounds preferred in the practice of the present invention are antibacterial ester compound of Formula (I) include N-alpha-cocoyl-L-arginine propyl ester, N alpha stearoyl-L-arginine methyl ester, N steaoryl-L-arginine ethyl ester hydrochloride. The term "cocoyl" is an abbreviation for coconut oil fatty acid residue, and chloride salts of these ester compounds hereinafter being referred to as arginine derivative compounds. The salt of the arginine derivative compound, ethyl lauroyl arginine, may be preferred for use in the practice of the present invention.

The oral composition of the invention includes a surfactant(s). Any known or to be developed in the art may be used, and the nature, ratio and content of the surfactant(s) used may be modified depending ion the specific end product desired. Nonionic surfactants useful in the present invention include condensates of sorbitan esters of fatty acids with ethylene oxide (polysorbates) such as sorbitan mono-oleate with from about 20 to about 60 moles of ethylene oxide and polysorbates. Zwitterionic surfactants that may be used include betaine surfactants and those disclosed in U.S. Pat. No. 5,180,577, incorporated herein by reference, alkyldimethyl betaines, such as decyl betaine 2-(N-decyl-N,N-dimethylammonio) acetate, cocobetaine or 2-(N-coc-N,N-dimethyl ammonio) acetate, myristyl betaine, palmityl betaine, lauryl, betaine, cetyl betaine, cetyl betaine, stearyl betaine, etc. The amidobetaines are exemplified by cocoamidoethyl betaine, cocoamidopropyl betaine, laurmidopropyl betaine and the like.

Surfactants useful in the practice of the present invention include nonionic and zwitterionic surfactants. Suitable nonionic surfactants useful in the present invention include poly (oxyethylene)-poly(oxypropyle-ne) block copolymers. Such copolymers are known commercially by the non-proprietary name of poloxamers, which name is used in conjunction with a numeric suffix to designate the individual identification of each copolymer.

Poloxamers may have varying contents of ethylene oxide and propylene oxide which results in poloxamers which have a wide range of chemical structures and molecular weights.

The surfactants may be present in any amount. Preferred amounts are about 0.1% to about 5% by weight or about 0.6% to about 2.0% by weight.

The composition may contain an abrasive, such as, for example, a silica compound, perlite, pumice, calcium carbonate, calcium carbonate, polymer particulates, dicalcium phosphate, alumina and precipitated silica. If a silica compound is selected, it may be one or more of the silicas known or developed in the art for use in various consumer products, such as a precipitated silica and/or a surface modified silica. The silica may be a silica coated with a glyceride of a fatty acid, for example, ricinoleic acid or the acids of castor oil.

Other silica abrasives that may be useful in the practice of the present invention include silica gels and precipitated amorphous silicas. These silicas are colloidal particles having an average particle size ranging from about 3 microns to about 12 microns, and more preferably between about 5 to about 10 microns and a pH range from 4 to 10 preferably 6 to 9 when measured as a 5% by weight slurry.

Illustrative of silica abrasives useful in the practice of the present invention are marketed under the trade designation SYLODENT® XWA by Davison Chemical Division of W.R. Grace & Co., Baltimore, Md. 21203. SYLODENT® 650 XWA, a silica hydrogel composed of particles of colloidal silica having a water content of 29% by weight averaging from about 7 to about 10 microns in diameter.

Other abrasives used in the practice of the present invention may include precipitated silicas having a mean particle size of up to about 20 microns, such as ZEODENT® 115, marketed by J.M. Huber Chemicals Division, Havre de Grace, Md. 21078, or SYLODENT® 783 marketed by Davison Chemical Division of W.R. Grace & Company.

The silica abrasive materials may be used individually as the sole abrasive in preparing the dental composition of the present invention or in combination with other known dentifrice abrasives such as sodium metaphosphate, dihydrated dicalcium phosphate, calcined alumina. The total quantity of abrasive present in the dentifrice compositions of the present invention is at a level of from about 5% to about 60% by weight, preferably from about 10% to about 55% by weight when the dentifrice composition is a toothpaste.

The ethoxylated hydrogenated castor oils used to precoat the silica compounds prior to their incorporation into the dentifrice of the present invention are prepared by hydrogenating castor oil and treating the hydrogenated product with from about 10 to about 200 moles of ethylene glycol. These ethoxylated hydrogenated castor oils are known by the nonproprietary name of PEG hydrogenated castor oils, in accordance with dictionary of the Cosmetics, Toiletries and Fragrance Association, 3rd Edition which name is used in conjunction with a numeric suffix to designate the degree of ethoxylation of the hydrogenated castor oil product, i.e., the number of moles of ethylene oxide added to the hydrogenated castor oil product. Suitable PEG hydrogenated castor oils include, PEG 16, 20, 25, 30, 40, 50, 60, 80, 100, and 200. In a preferred embodiment, the PEG 40 hydrogenated castor oil surfactant is CREMAPHOR RH40, a commercially available product from BASF-Wyandotte, Parsippany, N.J. Ethoxylated hydrogenated castor oil is coated on the silica compounds used in the preparation of the compositions of the present invention at a castor oil to silica weight ratio of about 1:10 to 1:2.

In some embodiments, it may be desirable to prepare a composition that does not contain a monohydric alcohol.

The compositions of the invention may contain numerous and varied other ingredients and may be in different delivery forms. For example, the composition may take the form of a tablet, a suspension, and emulsion, a lozenge, a confectionary, a chewing gum, a paste, a powder, a gel, a semi-solid stick, a spray, a film, a bead, a flake, a speckle, and a liquid.

If the composition is in the form of a film, it may contain a film forming polymer, such as a water soluble film forming polymer and a dispersible film-forming polymer. Such polymers may include any known/devel0ped in the art. Suitable polymers may include polyvinyl pyrrolidone, hydroxyethyl cellulose, hydroxypropyl methyl cellulose, hydroxyalkyl celluloses such as hydroxypropyl cellulose, carboxymethyl cellulose, starch, polyvinyl alcohol, sodium alginate, alginate esters, guar gum, xanthan gum, gelatin, polyethylene oxide, polyethylene glycol, carrageenan, pullulan, locust bean gum as well as water dispersible polymers such as polyacrylates, carboxyvinyl copolymers, methyl methacrylate copolymers and polyacrylic acid. Specifially, one may prefer a hydropropylmethyl cellulose polymer (29.1% methoxyl groups and 9% hydroxyproxyl group substitution) having a viscosity of about 1 to about 40 millipascal seconds (mPa.s) as determined as a 2% by weight aqueous solution of the HPMC at 20° C. using a Ubbelohde tube viscometer.

Preferably the selected polymer has a viscosity of about 1 to about 50 or 3 to about 20 mPa-s at 20° C.

The polymer may be incorporated in the film composition in amounts ranging from about 10 to about 60% by weight and preferably about 15 to about 40% by weight.

The composition may be in the form of a confectionary, such as a chewing gum or lozenge. If the form of a gum is desired, gum base materials suitable for use in the practice of this invention are well known in the art and include natural or synthetic gum bases or mixtures thereof. Representative natural gums or elastomers include chicle, natural rubber, jelutong, balata, guttapercha, lechi caspi, sorva, guttakay, crown gum, perillo, or mixtures thereof. Representative synthetic gums or elastomers include butadiene-styrene copolymers, polyisobutylene and isobutylene-isoprene copolymers.

The gum base may be incorporated in the gum at a concentration of about 10 to about 40% by weight and preferably about 20 to about 35% by weight. If desired, plasticizing/softening agents commonly used in chewing gum compositions are suitable for use in this invention, including gelatin, waxes and mixtures thereof in, for example, amounts of 0.1 to 5% by weight. Suitable non-cariogenic gums include kappa carrageenan, carboxymethyl cellulose, hydroxyethyl cellulose and the like.

If the form desired is a non-gum confenstionary, for example a lozenge bead or tablet, one may include as a carrier such as a non-cariogenic, solid water-soluble polyhydric alcohol (polyol) (such as mannitol, xylitol, sorbitol, malitol), hydrogenated starch hydrozylate, hydrogenated glucose, hydrogenated disaccharides or hydrogenated polysaccharides, in an amount of about 85 to about 95% by weight of the total composition. Emulsifiers such as glycerin, and tableting lubricants may be included Suitable lubricants for incorporation include vegetable oils such as coconut oil, magnesium stearate, aluminum stearate, talc, starch and Carbowax.

The lozenge, bead or tablet may optionally be coated with a material such as waxes, shellac, carboxymethyl cellulose, polyethylene/maleic anhydride copolymer or kappa-carrageenan to, for example, further increase the time it takes the tablet or lozenge to dissolve in the mouth.

Other ingredients that may be included in the composition of the invention include solid bases, sweeteners, sources of fluoride ions, of zinc ion, of copper ions, of silver ions; zinc citrate, zinc gluconate, additional anti-caries or antiadhesion agents, anti-inflammatory agents, antiplaque agents, sweeteners, flavorants, rheology modifiers, antitartar agents, humectants, plasticizers, solvents, botanical agents and herbs.

EXAMPLES

Example I

Mouthrinse

A mouthrinse of the present invention having a pH of 5.0 was prepared by dissolving in water each of the ingredients listed in Table I below with agitation in a glass mixing vessel.

TABLE I

| Ingredient | Wt. % |
| --- | --- |
| Ethyl lauroyl arginate HCl (ELAH) | 0.1 |
| Sorbitol | 10.0 |
| Glycerin | 10.0 |
| Propylene glycol | 7.0 |
| Polysorbate 20 | 0.8 |
| Cocoamidopropyl betaine | 0.8 |
| Sodium saccharin | 0.03 |
| Flavor | 0.10 |
| Water | Q.S. |

After 9 months at room temperature, the ELAH concentration was determined by Gas Chromatography--Mass Spectrometry to be unchanged at 0.1% by weight.

Using this mouthrinse, a double blind randomized clinical study was conducted in which 15 human subjects were asked to rinse for one minute with either the mouthrinse in Example I or a matching placebo (i.e., without ELAH) twice a day for 4 days while forgoing all other maintenance oral hygiene. There was a statistically significant reduction of 11.6% in plaque using the mouth rinse of Table I. The results of the study are recorded in Table II below.

TABLE II

Clinical efficacy of an alcohol-free mouthrinse

| Mouthrinse | Mean QHI* (SD)** | % Reduction relative to placebo |
| --- | --- | --- |
| Placebo | 2.51 (0.30) | — |
| 0.1% ELAH | 2.22 (0.22) | 11.6** |

*QHI = Quitley & Hein Index (Art recognized measure of plaque on teeth)
**Standard Deviation
**Significant at the 95% confidence level

Example II

Toothpaste

Toothpaste compositions containing ethyl lauroyl arginine HCL (ELAH) were prepared having the following ingredients:

TABLE III

| Ingredients | Composition (Wt. %) | | |
| --- | --- | --- | --- |
| | A | B | C |
| Polyethylene glycol 600 | 3 | 3 | 3 |
| PEG-40 castor oil | 6 | 6 | 0 |
| Hydroxyethyl cellulose | 1.0 | 1.0 | 1.0 |
| Xanthan | 0.2 | 0.2 | 0.2 |
| Sodium saccharin | 0.35 | 0.35 | 0.35 |
| Sodium fluoride | 0.243 | 0.243 | 0.243 |
| Sorbitol | 40 | 40 | 40 |
| Sodium hydroxide, 50% soln. | 0.5 | 0.5 | 0.5 |
| Titanium dioxide | 0.5 | 0.5 | 0.5 |
| ELAH | 0.5 | 0 | 0.5 |
| ZEODENT® 115 | 5 | 5 | 5 |
| ZEODENT® 165 | 2 | 2 | 2 |
| SYLODENT® XWA 650 | 15 | 15 | 15 |
| Polysorbate 20 | 1 | 1 | 1 |
| Cocomidopropyl betaine | 1 | 1 | 1 |
| Flavor | 0.72 | 0.72 | 0.72 |
| Water to make | 100 | 100 | 100 |

The dentifrice "Composition A" was prepared by dispersing the sorbitol in the water in a conventional mixer under agitation. Into the dispersion was added the xanthan, PEG-40 castor oil, sodium fluoride, hydroxyethyl cellulose, and sodium saccharine. The resultant mixture was agitated until a homogeneous gel phase was formed. Into the gel phase was added $TiO_2$ and sodium hydroxide to adjust the pH to 6.5. These ingredients were mixed until a homogenous phase was obtained. The mixture was then transferred to a high speed/vacuum mixer; wherein the PEG-40 castor oil coated silica compounds ZEODENT® 115, ZEODENT® 165, and SYLODENT® XWA 650 were added and the mixture mixed at high speed for 25 minutes, under vacuum from about 30 mm Hg. Finally, polysorbate 20, cocoamidobetaine, flavor and ELAH were added to the mixture and mixed for an additional 10 minutes. The resultant product was a homogenous, semisolid, extrudable paste or gel product.

For purposes of contrast, the procedure of the Example was repeated to prepare Composition B with the exception that ELAH was not included in the dentifrice formula. A second comparative composition, Composition C, was also prepared following the procedure of the Example with the exception that neither silica abrasive ZEODENT® 115 (Composition A) or the silica abrasive ZEODENT® 165 (Composition B) present in the dentifrice was coated with the PEG-40 castor oil.

The stability of the ELAH present in the prepared dentifrice composition A, B, C was measured by titrating a 0.015% wt. solution of the dentifrice with a 0.005N solution of sodiym lauryl sulfate (SLS). The recovery results are recorded in Table IV below.

TABLE IV

| Composition | % Recovery ELAH |
| --- | --- |
| A | 87.1 |
| B | 3.0 |
| C | 7.5 |
| ELAH (Palcebo) | 102.8 |

The antiplaque activity of Composition C was assessed using a flow cell model of the type disclosed in the Journal of Dental Research, vol. 73(II), pp. 1748-1755 (1994). Pooled human saliva was used as the bacterial source and single crystal geranium prisms as the oral surface model. Prior to exposure to bacteria, the surfaces were treated with a 2:1 dentifrice water slurry and then rinsed with artificial saliva (1 part porcine mucin 25 g/L, and 1 part saliva buffer solution) for 30 minutes under 1 mL/min flow conditions.

Composition A was assessed for overall plaque inhibition versus the comparative Composition B which did not contain ELAH, and Composition C in which the silica abrasive and thickener were not precoated with PEG-40 castor oil. The compositions were simultaneously run in the system. The lower plaque score the more effective the antiplaque agent. The results recorded in Table V below show a significant reduction in plaque effected by Composition A when compared to comparative Compositions B and C.

TABLE V

| Composition | Plaque Index | % reduction |
|---|---|---|
| A | 1.4237 | 17.5 |
| B | 1.7232 | — |
| C | 1.6705 | 3.2 |

The results recorded in Table V indicate that Composition A containing the PEG-40 castor oil coated silica compounds was more effective in plaque reduction than composition C which the silica compounds were not coated with the PEG-40 castor oil as well as Composition B which did not contain ELAH.

Example III

A series of films containing varying amounts of the arginine derivative compound they hydrochloride salt of ethyl lauroyl arginine designated Compositions A, B and C were prepared by using the ingredients listed in Table VI below. In preparing the film, the hydroxyl propylmethylcellulose polymer ingredient (Methocel E5LV) and carrageenan as added at a temperature of 70° C. to 90° C., to half the amount of total deionized water used, and the solution stirred for 20 minutes at a slow speed using IKA Labortechnik Model RW20DZMixer. The remaining amount of water maintained at room temperature (21° C.) was then added and the mixing continued for 40 minutes. To this solution was added the corn starch ingredient (Cerestar Polar Tex Instant 12640) and the mixture stirred for an additional 20 minutes until the starch was completely dispersed and a homogenous mixture was formed. To this mixture was added sucralose and mixed for 10 minutes after which the emulsifier Tween 80 was added and mixed for an additional 5 minutes. Thereafter, flavor was thoroughly mixed for an additional 30 minutes to form a flurry emulsion to which as a final step the hydrochloride salt of ethyl lauroyl arginine HCL (ELAH) dispersed in canola oil was slowly added until evenly dispersed in the film ingredient slurry. The emulsion was then cast on a polyethylene coated paper substrate and dried in a convection oven at 110° C. to form a solid thin (30 to 60 μm thick) film.

For purposes of comparison, the procedure of Example III was repeated to prepare a film composition designated Composition D with the exception that no ethyl lauroyl arginine HCL was incorporated in the film composition.

TABLE VI

| Ingredients | Composition (Wt. %) | | | |
|---|---|---|---|---|
| | A | B | C | D |
| HPMC | 41.0 | 41.0 | 38 | 41.0 |
| Carageenan | 0.50 | 0.50 | 0.50 | 0.50 |
| Corn Starch | 19.0 | 19.0 | 17 | 19.0 |
| Flavor | 25.0 | 25.0 | 18 | 25.0 |
| Tween 80 | 2.30 | 2.30 | 2.1 | 2.30 |
| Canola oil | 4.50 | 4.50 | 4.1 | 4.50 |
| Sucralose | 1.4 | 1.4 | 1.3 | 1.4 |
| Propylene glycol | 1.25 | 6.25 | 11.5 | 0 |
| ELAH | 0.50 | 2.5 | 5.0 | 0 |
| Water | Q.S. | Q.S. | Q.S. | Q.S. |

The antiplaque activity of Compositions A, B, C and D was assessed using a flow cell model of the type disclosed in the Journal of Dental Research, vol. 73(11), pp. 1748-1755 (1994) using human saliva as the bacterial source and single crystal germanium prisms as the oral surface model. After pretreatment of these surfaces with a precisely cut strip (10 mm×20 mm), they were rinsed with artificial saliva (1 part porcine mucin 25 g/L, and 1 part saliva buffer solution) prior to exposure to bacteria, and exposed to treatment in the flow cell. The plaque index of the deposits on the prisms was determined by infrared spectrophotometry.

Plaque Score

Compositions A, B and C were assessed for overall plaque inhibition versus the comparative Composition D which did not contain an antibacterial agent which was simultaneously run in the system. The lower the Plaque Index the more effective the antiplaque agent. The results recorded in Table VII below show a 30-40% reduction in plaque effected by Film Compositions A, B and C when compared to Folm Composition D.

TABLE VII

| Composition | Plaque Index | % reduction |
|---|---|---|
| A | 0.429 | 37.7 |
| B | 0.466 | 32.4 |
| C | 0.486 | 29.6 |
| D | 0.690 | — |

Example IV

A second series of film compositions designated E and F were prepared following the procedure of Example I, in which Composition E contained 5% by weight (dry film) ELAH, Composition F contained 5% by weight (dry film) ELAH and 1.5% by weight (dry film) zinc gluconate. For purposes of comparison, film Composition G prepared in the same manner as Film A but which contained no ELAH and Film Composition H, a commercially available breath freshening film were tested for antiplaque efficacy in the artificial mouth test model. The tests were run in parallel under identical conditions wherein 4 hydroxyapatitie discs (HAP) disks were coated with pellicle for two hours followed by additional 2 hours of bacteria attachment. The disks were mounted in a flow cell and 10 μmL solution of film (containing 150 mg film) were then passed over the surface of the disks for 1-2 minutes; water was passed over the disks for 10 minutes to wash. The flow cell was then connected to the artificial mouth chemostat circulator and incubated for 8-12 hours. The procedure was repeated 4 times, and thereafter the HAP disks were dismounted and bacteria on the disks were detached. The bacteria were quantified by optical density readings. The results of this test procedure are recorded in Table VIII below.

TABLE VIII

| Film Composition | Optical Density | | |
|---|---|---|---|
| | Mean | Standard Deviation | % Reduction |
| E | 0.23 | 0.02 | 31.2 |
| F | 0.20 | 0.03 | 38.9 |
| G | 0.33 | 0.05 | 0 |
| H | 0.38 | 0.38 | 1.0 |

The results in Table VIII show that antibacterial films of the present invention (Films E, F) effect a significant reduction in antiplaque formation when compared to films G, H that did not contain the arginine derivative compound.

Example V

The procedure of Example IV was repeated in which a series of film compositions designated J, K were prepared following the procedure of Example I in which Composition E contained 5% by weight (dry film) ELAH, Composition L contained 5% by weight (dry film) ELAH and 1.5% by weight (dry film) zinc gluconate. For purposes of comparison, Composition M contained 5% by weight (dry film) Triclosan, but no ELAH and Composition H was a placebo containing no ELAH or antibacterial ester compound.

The antiplaque efficacy of the films was evaluated following the artificial mouth model described in Example IV. The results of these tests are recorded in Table IX below.

TABLE IX

| Film Composition | Optical Density | | |
|---|---|---|---|
| | Mean | Standard Deviation | % Reduction |
| J | 0.23 | 0.02 | 31.2 |
| K | 0.20 | 0.03 | 38.9 |
| L | 0.23 | 0.03 | 30.6 |
| M | 0.33 | 0.05 | 0.0 |

The results recorded in Table IX indicate that ELAH is at least effective as Triclosan in reducing plaque formation when delivered to the oral cavity from a consumable film and that a combination of ELAH and a metal salt such as zinc gluconate provides antiplaque efficacy superior to Triclosan.

Example VI

A series of film compositions designated Compositions N, P, Q were prepared following the procedure of Example I, in which Composition N contained 0.50 by weight ELAH, Composition P contained 2.5% ELAH and Composition Q contained 5% by weight ELAH.

For purposes of comparison film Composition R was also prepared following the procedure of Example I except that no ELAH was incorporated in the film composition.

Film Compositions N, P, Q and R were evaluated for breath freshening efficacy by an in-vitro volatile sulfur compound (VSC) reduction assay. In this assay a known amount of film is dissolved in 3.0 milliliters (ml) of saliva in a glass vial. After incubation at 37° C. overnight, the headspace of the solution is sampled and analyzed for the VSC. The VSC assay results are presented in Table X below.

TABLE X

| Film Composition | VSC in the headspace | | |
|---|---|---|---|
| | Baseline | After 24 hours | VSC Reduction (%) |
| N | 27.3 | 23.90 | 12.5 |
| O | 27.3 | 18.36 | 32.8 |
| Q | 27.3 | 4.56 | 83.3 |
| R | 27.3 | 25.61 | 6.3 |

The VSC assay results recorded in Table X demonstrate the increase in VSC reduction as the concentration of the antibacterial ester ELAH in the film matrix is increased.

Example VII

TABLE XI

| Lozenge | |
|---|---|
| Ingredient | Wt. % |
| Saccharin | 0.15 |
| Magnesium Stearate | 0.40 |
| Glycerin | 1.0 |
| Ethyl lauroyl arginine | 0.5 |
| Flavor | 2.0 |
| Sorbitol | Q.S |

Example VIII

TABLE XII

| Bead | |
|---|---|
| Ingredient | Wt. % |
| Gelatin | 30 |
| Flavor | 45 |
| Vegetable oil | 22.5 |
| Aspartame | 0.2 |
| Ethyl lauroyl arginine | 1 |
| Food color | 0.002 |
| Flavor | 2.0 |
| Ethyl alcohol | 0.3 |
| Water | Q.S. |

Example IX

TABLE XIII

| Tablet | |
|---|---|
| Ingredient | Wt. % |
| Starch coated dicalcium phosphate | 40 |
| Cellulose | 20 |
| Glycerin | 12 |
| Sorbitol | 17 |
| Sodium saccharin | 0.2 |
| Flavor | 1 |
| Lechithin | 0.5 |
| Ethyl lauroyl arginine | 0.5 |
| Water | Q.S. |

Example X

TABLE XIV

Chewing Gum

| Ingredient | Wt. % |
|---|---|
| Gum base | 25 |
| Binder | 10 |
| Aspartame | 0.5 |
| Ethyl lauroyl arginine | 1 |
| Flavor | 2.0 |
| Titanium dioxide | 0.4 |
| Sorbitol/maltitol (50:50) | Q.S. |

We claim:

1. An oral care composition comprising:
   (a) a safe and effective amount of a compound represented by the formula (I):

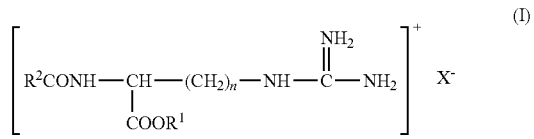

wherein $R^1$ and $R^2$ are independently selected from a hydrogen atom and an alkyl group and $X^-$ is an anion, and n is an integer of 1 to 25;
   (b) a surfactant; and
   (c) a silica compound coated with a fatty acid, wherein the fatty acid is ricinoleic acid.

2. The composition of claim 1, wherein the composition is free of a monohydric alcohol.

3. The composition of claim 1, wherein $R^1$ is an alkyl group having 1 to 25 carbon atoms.

4. The composition of claim 1, wherein $R^1$ is an alkyl group having 1 to 8 carbon atoms.

5. The composition of claim 1, wherein $R^2$ is an alkyl group having 1 to 50 carbon atoms.

6. The composition of claim 1, wherein $R^2$ is an alkyl group having 1 to 30 carbon atoms.

7. The composition of claim 1, wherein n is an integer of 1 to 10.

8. The composition of claim 1, wherein n is 3.

9. The composition of claim 1, wherein $X^-$ is selected from a hydrochloride anion, a sulfate anion, an acetate anion, a tartarate anion, and a citrate anion.

10. The composition of claim 1 wherein the compound is the hydrochloride salt of ethyl lauroyl arginine.

11. The composition of claim 1, wherein the compound is present at a concentration of about 0.02% to about 2% by weight of the composition.

12. The composition of claim 1, wherein the compound is present at a concentration of about 0.05% to about 25% by weight of the composition.

13. The composition of claim 1, wherein the surfactant is selected from a nonionic surfactant and a zwitterionic surfactant.

14. The composition of claim 1, further comprising a polyhydric alcohol.

15. The composition of claim 1, wherein the composition further comprises an uncoated abrasive.

16. The composition of claim 14, wherein the uncoated abrasive is selected from a silica compound, perlite, pumice, calcium carbonate, polymer particulates, and precipitated silica.

17. The composition of claim 1 having a form selected from a tablet, a lozenge, a confectionary, a chewing gum, a paste, a powder, a gel, a semi-solid stick, a spray, a film, a bead, a flake, a speckle, and a liquid.

18. The composition of claim 1, wherein the composition further comprises a solid base and a sweetener.

19. The composition of claim 1, wherein the composition is in the form of a film and further comprises a film-forming polymer selected from a water soluble film-forming polymer and a dispersible film-forming polymer.

20. The composition of claim 19, wherein the polymer is selected from a hydroxyalkyl cellulose polymer and a hydroxymethylpropyl cellulose.

21. The composition of claim 19, wherein the polymer is present in the composition in a concentration of about 10% to about 60% by weight of the composition.

22. The composition of claim 1, further comprising a metal salt.

23. The composition of claim 22, wherein the metal salt is selected zinc gluconate and zinc citrate.

* * * * *